United States Patent [19]

Schrock

[11] 4,245,131
[45] Jan. 13, 1981

[54] DIMERIZATION OF OLEFINS USING TANTALUM AND NIOBIUM CATALYSTS

[75] Inventor: Richard R. Schrock, Brighton, Mass.

[73] Assignee: Massachusetts Institute of Technology, Cambridge, Mass.

[21] Appl. No.: 54,211

[22] Filed: Jul. 2, 1979

Related U.S. Application Data

[63] Continuation of Ser. No. 32, Jan. 2, 1979, which is a continuation-in-part of Ser. No. 883,628, Mar. 6, 1978, abandoned.

[51] Int. Cl.³ ............................................. C07C 2/26
[52] U.S. Cl. ..................................... 585/511; 585/520
[58] Field of Search ............ 260/429 CY, 429 R, 440, 260/446, 447; 546/3, 4; 585/511

[56] References Cited

U.S. PATENT DOCUMENTS

| | | | |
|---|---|---|---|
| 3,932,477 | 1/1976 | Schrock | 260/429 R |
| 3,933,876 | 1/1976 | Tebbe | 260/429 R |
| 3,988,332 | 10/1976 | Schrock | 260/429 R |
| 3,992,472 | 11/1976 | Urry | 260/429 R |
| 4,021,429 | 5/1977 | Schrock | 260/429 R |
| 4,197,419 | 4/1980 | Schrock | 585/511 |

Primary Examiner—Curtis R. Davis
Attorney, Agent, or Firm—Paul J. Cook

[57] ABSTRACT

Tantalum and niobium catalysts or catalyst precursors of the formula:

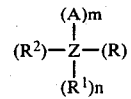

wherein R is cyclopentadienyl, which can be substituted with methyl up to five positions, or neopentylidene, $R^1$ is neopentyl or benzyl, n is 0 or 1, $R^2$ is neopentylidene, benzylidene, tetramethylene, or 2,3-dimethyltetramethylene, A is halo or a moiety of the formula $YR^3R^4R^5$ wherein Y is a group 5 element including N, P, As, Sb and Bi and $R^3$, $R^4$, $R^5$ can be the same or different and are $C_1$–$C_4$ alkyl, aralkyl such as naphthyl, neophyl, tolyl or xylyl, aryl such as benzyl or phenyl or bipyridyl and Z is tantalum or niobium. The compounds selectively dimerize 1-olefins to 1-butenes; m = 1 or 2.

12 Claims, No Drawings

DIMERIZATION OF OLEFINS USING TANTALUM AND NIOBIUM CATALYSTS

The government has rights in this invention pursuant to Gret No. CHE 76-07410 and IPA-0010 awarded by the National Science Foundation.

REFERENCE TO RELATED APPLICATION

This application is a continuation of application Ser. No. 32, filed Jan. 2, 1979, which is a continuation-in-part of application Ser. No. 883,628, filed Mar. 6, 1978, and now abandoned.

BACKGROUND OF THE INVENTION

This invention relates to catalysts or catalyst precursors for forming 1-butenes from a 1-olefin reactant.

Prior to the present invention, there have been no known homogeneous catalysts for converting a terminal olefin selectively to a 1-butene or 2,3-disubstituted 1-butene at room temperature or above. Known homogeneous dimerization catalysts readily isomerize the initially formed 1-butene to the thermodynamically more stable internal butene. It is also known that heterogeneous catalysts such as chromocene on alumina or silica product 1-butene from ethylene. In addition, other selected dimerization reactions are known. However, these reactions generally are successful for only one olefin, e.g., the use of $KC_8$ to dimerize propylene selectively to 4-methyl-1-pentene.

Accordingly, it would be desirable to provide a homogeneous catalyst system for selectively forming 1-butenes which can be used with any one of a plurality of 1-olefin feed compositions.

SUMMARY OF THE INVENTION

This invention provides a class of tantalum or niobium catalysts or catalyst precursors for dimerizing 1-olefins to 1-butenes selectively. The catalysts are useful with $C_2$ to $C_4$ olefins and particularly with ethylene to produce substantially pure 1-butene. The catalysts are homogeneous in that they are in the same phase as the reactants under the conditions utilized in the reaction.

The catalysts of this invention are represented by the formula:

$$(R^2)-Z-(R) \quad \text{with} \quad (A)_m \text{ above and } (R^1)_n \text{ below}$$

wherein R is cyclopentadienyl, $C_5H_xMe_{5-x}$, wherein x is an integer from 0 to 5, or neopentylidene, $R_1$ is benzyl or neopentyl, n is 0 or 1, $R^2$ is neopentylidene, benzylidene, tetramethylene or 2,3-dimethyltetramethylene, A is halo including chloro, bromo, iodo and fluoro or a moiety of the formula $YR^3R^4R^5$ wherein Y is a group 5 element including N, P, Sb, and Bi and $R^3$, $R^4$, and $R^5$ can be the same or different and $C_1$-$C_4$ alkyl, aralkyl, i.e. naphthyl, neophyl, toluyl or xylyl, aryl, i.e. benzyl or phenyl, or bipyridyl and Z is tantalum or niobium; m = 1 or 2.

When A is $YR^3R^4R^5$, the compounds of this invention are prepared in accordance with the reaction I. (m = 2)

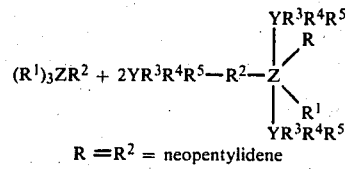

$R = R^2$ = neopentylidene

In accordance with reaction I, a tantalum catalyst of this invention is prepared as follows:

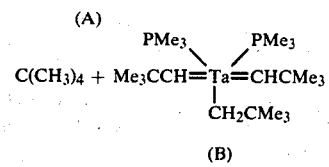

The reaction is conducted in an inert solvent such as pentane, benzene, decane or the like, at a temperature between about 0° and 150° C., preferably between about 20° and 40° C. Water and oxygen must be excluded. An inert atmosphere is required. The product (B) can be recovered by crystallization.

The reaction II can also be conducted in the presence of a $C_2$-$C_4$ olefin such as ethylene. The product (B) reacts instantly with the olefin to form a substantially pure 1-olefin dimer which in the case of ethylene is 1-butene. In this reaction, compound B functions as a precursor to a catalyst which effects the dimerization since, during the reaction, the two neopentylidene ligands and the neopentyl ligand are cleaved off. The reaction can be conducted at atmospheric pressure or preferably at an elevated pressure, usually at a pressure between 45 and 60 psi. At the elevated temperatures and pressures, reaction rates are substantially increased. The compound A or its niobium analog is made by the process set forth in U.S. Pat. No. 3,988,332 which is incorporated herein by reference.

The compounds of this invention wherein A is halo and R is cyclopentadienyl are prepared by the following general reaction wherein A is chloro(III). The same reaction scheme applies when A is bromo, fluoro, and/or iodo.

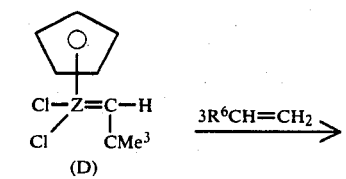

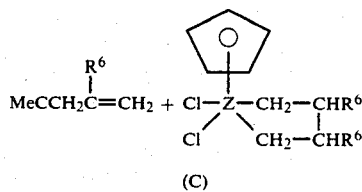

wherein $R^6$ is hydrogen, methyl or ethyl. The compounds (C), in the presence of a $C_2$-$C_4$ olefin, catalytically effect dimerization of the olefin to the corresponding 1-butene. The reaction of compound D and the olefin is effected in a dry, oxygen-free, inert solvent such as pentane, benzene, decane or the like, at a temperature between about 0° and 200° C., preferably between about 20° and 100° C. and at a pressure between about 15 psi and 1500 psi, preferably between about 45 psi and 60 psi. The olefin dimer is recovered by distillation after the reaction has been allowed to proceed to completion as indicated by gas chromatography.

The starting meterial (D) can be prepared by reacting either tantalum pentachloride or niobium pentachloride with $Zn(CH_2CMe_3)_2$ at a temperature between about 20° and 40° C. in toluene or pentane to form the compound: $(Me_3CCH_2)_2ZCl_3$. The latter compound then is reacted with $TlC_5Me_xH_{5-x}$ such as $TlC_5Me_5$ or $LiC_5Me_xH_{5-x}$ such as $LiC_5Me_5$ wherein X is 0 to 5 at a temperature of between about 20° and 40° C. in toluene or diethyl ether to form the starting material (D). Representative compounds prepared by this invention include:

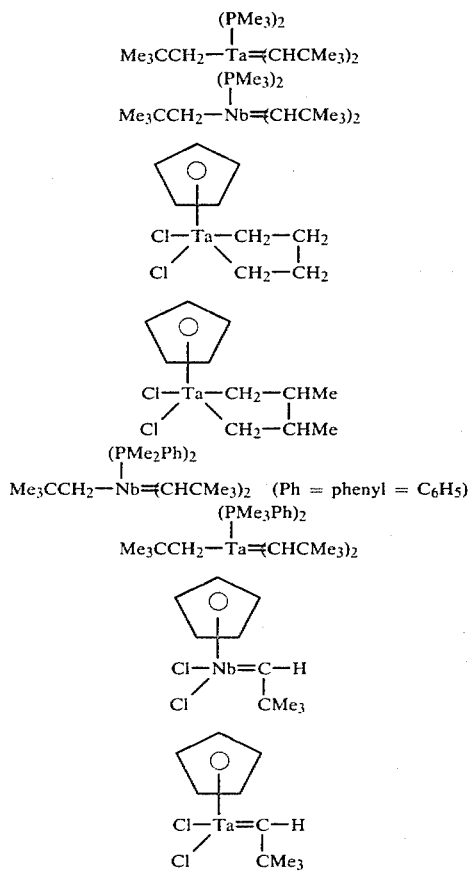

In the process of this invention, the following group 5 donors can be employed: $PMe_3$, $NMe_3$, $BiMe_3$, $PMe_2Ph$, $AsMe_3$, $P(OMe)_3$ or an optically active phosphine of the formula $PR^1R^2R^3$ when $R^1R^2$ and $R^3$ are defined above.

The catalysts and catalyst precursors of this invention provide substantial advantages over the prior art in that the reactants and catalysts or catalyst precursors can enter the reaction in a single phase and the products produced are substantially pure 1-olefin dimers, i.e., at least about 95 weight percent pure.

SPECIFIC EMBODIMENTS OF THE INVENTION

The following examples illustrate the present invention and are not intended to limit the same nor be construed as fully delineating the scope of this discovery.

In order to avoid the presence of molecular oxygen and moisture, all experiments below were carried out in an atmosphere of dry nitrogen gas.

EXAMPLE I

This example illustrates the method for making the compounds of the formula

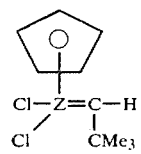

wherein Z is Ta or Nb.

4.3 grams of $Ta(CH_2CMe_3)_2Cl_3$ (or 3.4 grams of $Nb(CH_2CMe_3)_2Cl_3$) was dissolved in toluene and 2.4 grams of $TlC_5H_5$ added and reacted therewith at 25° C. for 24 hours. A residue, in each case, was obtained after filtering off TlCl and removing all solvent in vacuo. It was recrystallized from pentane/toluene (5:1) at $-40°$ C. to give a 70 weight percent yield of the Ta compound and 15 weight percent yield of the Nb compound. (Calcd for $TaC_{10}H_{15}Cl_2$: C, 31.03; H, 3.90; Cl, 18.32. Found: C, 31.17; H, 4.05; Cl, 18.30. Calcd for $NbC_{10}H_{15}Cl_2$: C, 40.17; H, 5.05; Cl, 23.71. Found: C, 40.19; H, 5.16; Cl, 23.66.). The $^1H$ and $^{13}C$ NMR spectra for both compounds are entirely consistent with formulation as neopentylidene complexes. [$\delta^{13}C_\alpha = 246$ ppm (Z=Ta) downfield of internal tetramethylsilane standard in $C_6D_6$; $^1J_{C\alpha H} = 84$ Hz]. A molecular weight measurement suggests the Ta compound is a monomer in benzene. The Ta compound is thermally stable, unchanged after 3 h at 150° C. in benzene is a sealed tube or sublimation at $1\mu$ and 65° C.), but reacts readily with moist air. As in other tantalum alkylidene complexes, the neopentylidene $\alpha$-carbon atom is believed to be nucleophilic, e.g., it reacts with HCl at $-78°$ C. in toluene to give Ta $(\eta^5-C_5H_5)Cl_3(CH_2CMe_3)$ in 95% isolated yield.

EXAMPLE II

This example illustrates the method for making the compounds of the formula

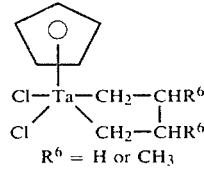

$R^6 = H$ or $CH_3$

Ethylene (45 psi) reacted readily with 3.88 grams (10 m mol) $Ta(\eta^5-C_5H_5)(CHCMe_3)Cl_2$ partially dissolved in 20 ml pentane at 25° C. The red color first deepened, then lightened to yellow-orange in 3-5 min as orange crystals of $(\eta^5-C_5H_5)Cl_2\overline{TaCH_2CH_2CH_2CH_2}$ fell from solution. The product was isolated in 95% yield by filtration. (Calcd for TaC$_9$H$_{13}$Cl$_2$: C, 28.98; H, 3.51; Cl, 19.01. Found: C, 29.03; H, 3.63; Cl, 19.17.)

The −40° C. 60 MHz $^1$H nmr spectrum of ($\eta^5$—C$_5$H$_5$)Cl$_2$TaCH$_2$CH$_2$CH$_2$CH$_2$ in toluene-d$_8$ under 1 atm of ethylene shows a $\eta^5$—C$_5$H$_5$ resonance at τ 4.60, a small peak for free, dissolved ethylene at τ 4.75, and two broad peaks (ca. 20 Hz wide) and two sharper peaks (ca. 10 Hz wide) at τ 6.35, 7.15, 7.95 and 8.10, respectively, of approximately equal area, and a total area of eight protons vs. $\eta^5$—C$_5$H$_5$. On warming to 40° C., the broad pair coalesces with the sharper pair to give two peaks at τ 7.25 and 7.60; the peak for free ethylene remains sharp and does not shift appreciably.

The 67.89 MHz gated decoupled $^{13}$C spectrum of ($\eta^5$—C$_5$H$_5$)Cl$_2$TaCH$_2$CH$_2$CH$_2$CH$_2$ in C$_6$D$_6$ was measured at 25° C. The two triplet resonances due to the two types of carbon atoms in the tetramethylene-metal ring are found at 89.7 and 33.5 ppm downfield of tetramethylsilane with $^1J_{CH}=123\pm2$ and $126\pm2$ Hz, respectively. The doublet ($^1J_{CH}=181$ Hz) due to $\eta^5$—C$_5$H$_5$ is found at 112.8 ppm.

($\eta^5$—C$_5$H$_5$)Cl$_2$TaCH$_2$CH$_2$CH$_2$CH$_2$ has also been characterized by chemical reactions. It reacts with Br$_2$ in diethyl ether at −78° C. to give 1,4-dibromobutane (0.83 per Ta) and 1,2-dibromoethane (0.18 per Ta), and with CO (3 atm) in diethyl ether at −78° C. (followed by warming to 25° C.) to give cyclopentanone (0.50 per Ta) and nearly insoluble TaCp($\eta^5$—C$_5$H$_5$)Cl$_2$(CO)$_2$ (0.55 per Ta; $\nu_{co}$(cm$^{-1}$)=2945 s, 1962 s).

The organic product of this reaction is almost exclusively 4,4-dimethyl-1-pentene (Table I). The yield of 3,3-dimethyl-1-butene, the metathesis product, is insignificant and the yield of tert-butylcyclopropane must be ≲5%.

Propylene (45 psi) reacts with Ta($\theta^5$—C$_5$H$_5$)(CHCMe$_3$)Cl$_2$ in pentane at 0° in two hours to give a precipitate of ($\eta^5$—C$_5$H$_5$)Cl$_2$TaCH$_2$CHMeCHMeCH$_2$ which was isolated by filtration in 75% yield. In the absence of propylene this compound decomposes in the solid state or in solution (in pentane, for example) at ≳25° C.

The proton decoupled 22.63 MHz $^{13}$C nmr spectrum of ($\eta^5$—C$_5$H$_5$)Cl$_2$TaCH$_2$CHMeCHMeCH$_2$ in toluene-d$_8$ at 7° C. shows singlet resonances at 113.5 ($\eta^5$—C$_5$H$_5$), 95.6 (C$_\alpha$), 49.7 (C$_\beta$), and 24.7 (C$_\gamma$); C$_\alpha$ is a triplet ($^1J_{CH}=123\pm2$ Hz), C$_\beta$a doublet ($^1J_{CH}=126\pm2$ Hz), and C$_\gamma$a quartet ($^1J_{CH}=128\pm2$ Hz) in the 67.89 MHz gated decoupled $^{13}$C spectrum.

The major organic product of this reaction is 2,4,4-trimethyl-1-pentene (Table I).

The major organic product of the reaction of Ta($\eta^5$—C$_5$H$_5$)(CHCMe$_3$)Cl$_2$ with styrene and cis-3-hexene results from an analogous, selective insertion of neopentylidene into an olefinic C—H bond (Table I). A qualitative comparison suggests that the rate of reaction of these four olefins with the Ta compound decreases in the order ethylene>propylene>styrene>>cis-3-hexene. The fact that β,β-dimethylstyrene did not react appreciably under conditions where cis-3-hexene was consumed is consistent with this general trend. The reaction of the Nb compound with ethylene also gives 4,4-dimethyl-1-pentene, but in lower yield.

It is believed that the olefin adds to the metal-neopentylidene double bond to give one metallocyclobutane intermediate selectively (e.g., 1, 2 and 3, Scheme I), the one which is consistent with the neopentylidene ligand's nucleophilic properties. A specific hydrogen atom shift from C$_\beta$ to the tertbutyl-substituted C$_\alpha$ in 1, 2, and 3 is one means of generating the observed product.

TABLE I

Products of the Reaction of the Ta Compound and the Nb Compound with Olefins$^a$

| Z | Olefin | Products |
|---|---|---|
| Ta | CH$_2$=CH$_2$ (45 psi) | 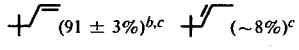 (91 ± 3%)$^{b,c}$   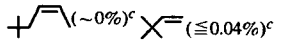 (~8%)$^c$ <br> 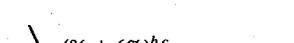(~0%)$^c$   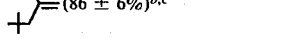(≲0.04%)$^c$ |
| Ta | CH$_3$CH=CH$_2$ (45 psi) | 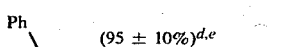 (86 ± 6%)$^{b,c}$ |
| Ta | PhCH=CH$_2$ (3 mol in C$_6$D$_6$) |  (95 ± 10%)$^{d,e}$ |
| Ta | cis-3-Hexenes (neat, 120° C.) |  (or isomers; >50%)$^f$ |
| Nb | CH$_2$=CH$_2$ (45 psi) | (62 ± 3%)$^{b,c}$ |

$^a$Solvent = mesitylene, pentane, or C$_6$D$_6$; T = 25° C. unless otherwise noted. Minor product yields were measured only for the first example.

$^b$Identified by GLC yield and $^1$H NMR comparison (in C$_6$D$_6$) with an authentic sample.

$^c$GLC yield based on internal standard (a saturated hydrocarbon).

$^d$Proposal based on $^1$H NMR comparison (in C$_6$D$_6$) with the spectrum of trans-propenylbenzene.

$^e$Yield determined in C$_6$D$_6$ by $^1$H NMR vs. internal cyclohexane standard.

$^f$The mass and $^1$H NMR spectra are consistent with the major olefin product being one of this type.

SCHEME I
Proposed Metallocyclobutane Intermediates

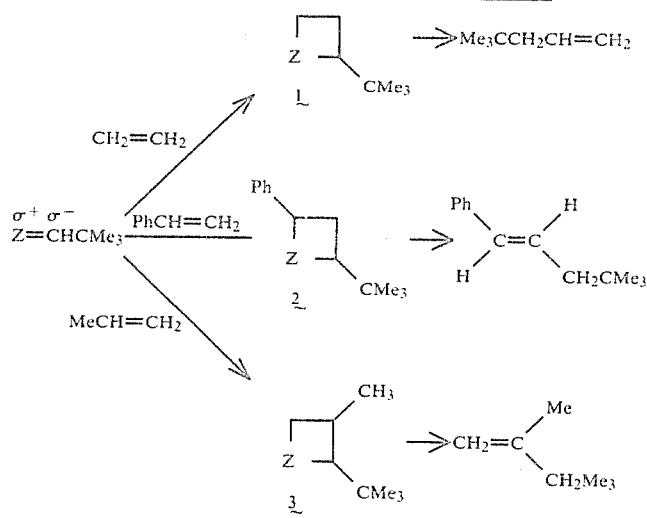

EXAMPLE III

This example illustrates the method for making the compounds of the formula:

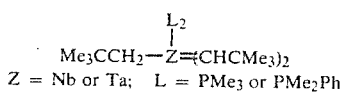

$Z = Nb$ or $Ta$;   $L = PMe_3$ or $PMe_2Ph$

To 25 ml of pentane containing 4.6 grams of $Ta(CH_2CMe_3)_3(CHCMe_3)$ was added 1.7 grams of $PMe_3$. After 24 hours, the pentane and excess $PMe_3$ were removed in vacuo to give 5.4 grams of virtually pure $Ta(CH_2CMe_3)(CHCMe_3)_2(PMe_3)_2$ as a yellow-orange residue. It may be recrystallized from pentane as orange crystals.

One mole per Ta of the organic product, neopentane, was identified and measured by gas chromatography.

The product is monomeric in cyclohexane (by cryoscopic measurement).

The 270 MHz $^1H$ nmr spectrum of this product in $C_6D_6$ shows three $CMe_3$ peaks at $\tau$ 8.795, 8.803 and 8.844, a $CH_2$ triplet ($J_{HP}=19$ Hz) at $\tau$ 9.39, two $=CH-$ peaks at $\tau$ 7.92 and 3.07, and a $PMe_3$ triplet ($J_{HP}=2.4$ Hz) at 96 8.68. The 67.89 MHz gated decoupled $^{13}C$ spectrum in $C_6D_6$ shows the two $=CH-$ carbon atoms at 274 and 246 ppm downfield of $SiMe_4$ ($^1J_{CH}=95$ Hz and 85 Hz, respectively), along with characteristic peaks for the other carbon atoms in this compound.

A similar reaction of 0.46 grams of $Ta(CH_2CMe_3)_3(CHCMe_3)$ with 0.26 grams of $PMe_2Ph$ in 10 ml of hexane at 60° C. for two days gave $Ta(CH_2CMe_3)(CHCMe_3)_2(PMe_2Ph)_2$ in virtually quantitative yield. It was purified by recrystallization from hexane. Its $^1H$ and $^{13}C$ nmr spectra show all of the important and essential features found in the corresponding spectra of the $PMe_3$ compound described above.

The method of forming the corresponding Nb compounds is virtually identical to that for $Z=Ta$ except the reaction of L ($PMe_3$ of $PMe_2Ph$) with freshly prepared $Nb(CH_2CMe_3)_3(CHCMe_3)$ is complete within one hour at the most in each case. $Nb(CH_2CMe_3)_3(CHCMe_3)$ is prepared by mixing $Nb(CH_2CMe_3)_3Cl_2$ and two moles of $LiCH_2CMe_3$ in pentane at $-78°$ C. followed by warming to 0° C. for 15 min. Each is isolated as in the respective Ta cases and purified by recrystallization from pentane. Their $^1H$ and $^{13}C$ nmr spectra show all the important and essential features found in the spectrum of $Ta(CH_2CMe_3)(CHCMe_3)_2(PMc_3)_2$ above.

EXAMPLE IV

This example illustrates the dimerization of ethylene to 1-butene by the catalyst precursor $Ta(CH_2CMe_3)(CHCMe_3)_2$ $(PMe_3)_2$.

A stirred solution of 0.20 grams of $Ta(CH_2CMe_3)(CHCMe_3)_2(PMe_3)_2$ in 20 ml of pentane at 30° C. in a pressure bottle was treated with ethylene maintained at a pressure of 60 psi. The starting compound rapidly reacts and the $C_5$ groups are cleaved off as neopentylethylene (identified by gc/mass spectroscopic comparison with authentic sample). The solution takes up ethylene steadily at the rate of approximately 1 mmole $min^{-1}$ per mole of Ta and the solution's volume steadily increases. After 8 hours, the volatiles were removed in vacuo. Analysis by gas chromatography showed (in addition to pentane solvent) primarily 1-butene with <5% 2-butenes and only traces of higher boiling products. No additional higher boiling products were found by gas chromatography in the catalytic reaction before transferring the volatiles.

The dimerization reaction will continue indefinitely if molecular oxygen and water are excluded. At higher temperatures (approximately 80° C.) and ethylene pressures (approximately 1500 psi) the rate increases markedly. These conditions are preferred for maximum rate of production of 1-butene.

EXAMPLE V

This example illustrates the dimerization of propylene to 2,3-dimethyl-1-butene by $(\eta^5-C_5H_5)Cl_2Ta\overline{CH_2CHMeCHMeCH_2}$.

$Ta(\eta^5-C_5H_5)(CHCMe_3)Cl_2$ (0.075 grams) in 10 ml decane at 45° C. reacts rapidly with propylene (45 psi) to give 2,4,4-trimethyl-1-pentene (see Table 1) and ($\eta^5$—C$_5$H$_5$)Cl$_2$TaCH$_2$CHMeCHMe CH$_2$ stoichiometrically. Under these conditions, 2,3-dimethyl-1-butene forms catalytically; it comprises 93% of the product mixture as determined by monitoring the catalytic reaction by gas chromatography. A second primary product (5% of the mixture) is 2-methyl-1-pentene. A third primary product (2% of the mixture) is tetramethylene. The same products in the same amounts are formed catalytically starting with previously isolated ($\eta^5$—C$_5$H$_5$)Cl$_2$TaCH$_2$CHMeCHMeCH$_2$.

At 45° C., the 2,3-dimethyl-1-butene is formed at a rate of about two mols per Ta per hour. The rate can be increased markedly by increasing the temperature and propylene pressure.

EXAMPLE VI

This example illustrates the dimerization of 1-butene by ($\eta^5$-C$_5$H$_5$)Cl$_2$TaCH$_2$CHEtCHEtCH$_2$.

Ta($\eta^5$—C$_5$H$_5$)(CHCMe$_3$)Cl$_2$ in 10 ml decane at 45° C. reacts with 1-butene (10 psi) to give the expected cleavage product, 2-ethyl-4,4-dimethyl-1-pentene, and an active catalyst (presumably thermally unstable ($\eta^5$—C$_5$H$_5$)Cl$_2$TaCH$_2$CHEtCHEtCH$_2$) for the dimerization of 1-butene to 2,3-diethyl-1-butene (identified by gc/mass spectroscopey: parent ion 126, base peak 57). The production of 2,3-diethyl-1-butene can be followed by gas chromatography. No other butenes were found.

EXAMPLE VII

This example illustrates the method for making the compound of the formula

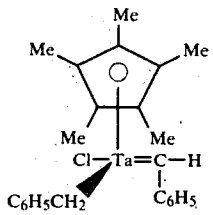

To 7.1 grams of orange Ta(CH$_2$C$_6$H$_5$)$_3$Cl$_2$ (prepared from TaCl$_5$ and 1.5 Zn(CH$_2$C$_6$H$_5$)$_2$ in toluene) in tetrahydrofuran was added 2.1 grams of LiC$_5$Me$_5$. After stirring overnight, the solvent was removed in vacuo and the residue was extracted with 50 ml benzene. Pentane (50 ml) was added and the solution stood at room temperature for 1 day to give 4.8 grams (68%) of Ta($\eta$-$^5$—C$_5$Me$_5$)(CH$_2$C$_6$H$_5$)(CHC$_6$H$_5$)Cl as a red powder. $^1$H nmr ($\delta$, C$_5$D$_6$, 90 MHz, 35°): 1.82 (s, 15, CH$_3$), 2.26 (Ab quartet, 2, CH$_2$, J=12 and 7 Hz), 6.73 (s, 1, =CH), and 6.58–7.38 (m, 10, C$_6$H$_5$). $^1$H nmr ($\delta$, C$_6$D$_6$, 270 MHz, 25°): 1.789 (s, CH$_3$), 2.257 (AB quartet, CH$_2$, J=11.7 and 30.9 Hz), 6.706 (s, =CH), and 6.855–6.965, 7.126–7.213, and 7.325–7.352 (m, C$_6$H$_5$ and C$_6$H$_5$').

$^{13}$C nmr ($\delta$, C$_6$D$_6$, gated $^1$H, 67.89 MHz, 25°): 11.4 (CH$_3$), 64.4 (1:1:1 t, overlapping d from splitting by diasterotopic protons, CH$_2$), 115.6 (s, C$_5$(CH$_3$)$_5$), phenyl regin complex and suggestive of two inequivalent phenyl groups, 148.4 (s, C$_\beta$ of benzylidene), and 221.5 (d, =CH, $^1$J$_{CH;b}$ =85 Hz).

IR (cm$^{-1}$, Nujol/NaCl): 3050 s, br; 3010 s, shoulder; 1940 w, br; 1870 w, br; 1795 w, br; 1730 2, br; 1650 w, br; 1590 s, br; 1485 vs, sh; 1290 w, br; 1195 s, br; 1175 vw, shoulder; 1155 vw, shoulder; 1060 m, shoulder; 1025 s, br; 930 w, sh; 900 w, br; 800 s, br; 755 vs, br; 730 m, sh, shoulder; 695 vs, sh.

EXAMPLE VIII

This example illustrates the method for preparing a compound of the formula

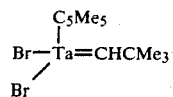

Pure Ta(CH$_2$CMe$_3$)$_2$Br$_3$ (2.70 g) was dissolved in 50 ml of ether and 0.70 g of LiC$_5$Me$_5$ added. The flask was covered with foil and stirred for 1 h. The ether was removed in vacuo and the residue was extracted into 125 ml of pentane. The extract was filtered and stood at −30° overnight to give 1.45 g of small red needles. Decreasing the volume afforded 0.35 g additional product; total yield=1.80 g (56%). The compound is benzene is red by transmitted light but blue-purple by reflected light.

$^1$H NMR ($\tau$, C$_6$D$_6$): 7.96 (s, 15, C$_5$Me$_5$), 8.54 (s, 18, CH$_2$CMe$_3$), 9.35 (s, 4, CH$_2$CMe$_3$).

TaCp''(CH$_2$CMe$_3$)$_2$Br$_2$ (0.80 g) was dissolved in minimal CDCl$_3$ and the solution was stood in the dark for two days. The solvent was removed and the residue was doubly recrystallized from minimal pentane at −30°; yield 0.40 g (57%). (C$_p$''=C$_5$Me$_5$)

$^1$H NMR ($\tau$, C$_6$D$_6$): 5.18 (s, 1, CHCMe$_3$), 7.88 (s, 15, C$_5$Me$_5$) 8.83 (s, 9, CHCMe$_3$). −C NMR (ppm, C$_6$D$_6$, $^1$H gated decoupled): 249 (d, CHCMe$_3$, $^1$J$_{CH}$=77 Hz), 119 (s, C$_5$Me$_5$), 48.2 (s, CHCMe$_3$), 33.2 (q, CHCMe$_3$, $^1$J$_{CH}$=126 Hz), 13.2 (q, C$_5$Me$_5$, $^1$J$_{CH}$=128 Hz).

I claim:

1. The process of forming a 1-butene selectively which comprises contacting a C$_2$ to C$_4$ olefin with the catalyst of the formula

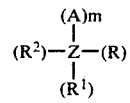

wherein R is cyclopentadienyl, C$_5$H$_x$Me$_{5-x}$, wherein x is an integer from 0 to 5, or neopentylidene, R$^1$ is neopentyl or benzyl, n is 0 or 1, R$^2$ is neopentylidene, benzylidene, tetramethylene or 2, 3-dimethyltetramethylene, A is halo or a moiety of the formula YR$^3$R$^4$R$^5$ wherein Y is a group 5 element and R$^3$, R$^4$ and R$^5$ can be the same or different and are C$_1$–C$_4$ alkyl, aralkyl, aryl or bipyridyl and Z is tantalum or niobium: m=1 or 2.

2. The process of claim 1 for forming a 1-butene selectively wherein Z is tantalum.

3. The process of claim 1 for forming a 1-butene selectively wherein Z is niobium.

4. The process of forming a 1-butene selectively which comprises contacting a C$_2$ to C$_4$ olefin with the catalyst of the formula

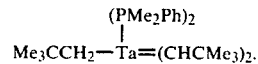

5. The process of forming a 1-butene selectively which comprises contacting a C$_2$ to C$_4$ olefin with the catalyst of the formula

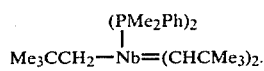

6. The process of forming a 1-butene selectively which comprises contacting a $C_2$ to $C_4$ olefin with the catalyst of the formula

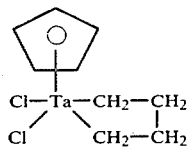

7. The process of forming a 1-butene selectively which comprises containing a $C_2$ to $C_4$ olefin with the catalyst of the formula

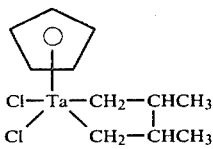

8. The process of forming a 1-butene selectively which comprises contacting a $C_2$ to $C_4$ olefin with the catalyst of the formula

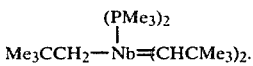

9. The process of forming a 1-butene selectively which comprises contacting a $C_2$ ;1 to $C_4$ olefin with the catalyst of the formula

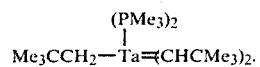

10. The process of forming a 1-butene selectively which comprises contacting a $C_2$ to $C_4$ olfin with the catalyst of the formula

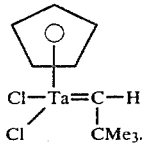

11. The process of forming a 1-butene selectively which comprises contacting a $C_2$ to $C_4$ olefin with the catalyst of the formula

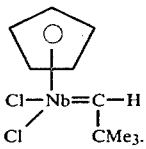

12. The process of forming a 1-butene selectively which comprises contacting a $C_2$ to $C_4$ olefin with the catalyst of the formula

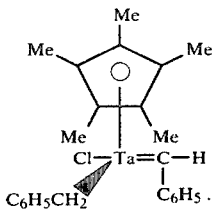

* * * * *